(12) United States Patent
Parks et al.

(10) Patent No.: US 8,912,151 B2
(45) Date of Patent: Dec. 16, 2014

(54) METHOD OF TREATING HEMORRHOIDS USING MACROCYCLIC LACTONE COMPOUND

(75) Inventors: L. Dean Parks, Ocala, FL (US); Jeffrey D. Parks, Ormond Beach, FL (US)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 13/823,226

(22) PCT Filed: Oct. 14, 2011

(86) PCT No.: PCT/US2011/056311
§ 371 (c)(1),
(2), (4) Date: Mar. 14, 2013

(87) PCT Pub. No.: WO2012/054328
PCT Pub. Date: Apr. 26, 2012

(65) Prior Publication Data
US 2013/0178433 A1    Jul. 11, 2013

Related U.S. Application Data

(60) Provisional application No. 61/394,895, filed on Oct. 20, 2010.

(51) Int. Cl.
| | | |
|---|---|---|
| *A61K 31/70* | (2006.01) | |
| *A61K 31/7048* | (2006.01) | |
| *A61K 31/365* | (2006.01) | |
| *A61K 9/00* | (2006.01) | |
| *A61K 9/06* | (2006.01) | |

(52) U.S. Cl.
CPC ........... *A61K 31/7048* (2013.01); *A61K 31/365* (2013.01); *A61K 9/0031* (2013.01); *A61K 9/06* (2013.01)
USPC ........................................................... 514/30

(58) Field of Classification Search
CPC ................................................. A61K 31/7048
See application file for complete search history.

(56) References Cited

U.S. PATENT DOCUMENTS

| | | |
|---|---|---|
| 2008/0167375 A1 | 7/2008 | Weidner |
| 2009/0286866 A1 | 11/2009 | Segura-Orsoni et al. |
| 2010/0173021 A1 | 7/2010 | Hahn et al. |

OTHER PUBLICATIONS

Supplemental European Search Report of counterpart European Application No. 11834898.6, Oct. 2013.
Fusco et al., "Case Report: Non-Oral Treatment with Ivermectin for Disseminated Strongyloidiasis", The American Journal of Tropical Medicine and Hygiene, vol. 83, No. 4, Oct. 5, 2010, pp. 879-883 The whole document.
International Search Report and Written Opinion of International Search Authority of PCT/US2011/056311, Feb. 2012.

*Primary Examiner* — Elli Peselev
(74) *Attorney, Agent, or Firm* — GUSPA Technology Law Associates, P.A.; Yi Li

(57) ABSTRACT

A method of treating hemorrhoids is disclosed. The method includes locally administering a composition including an effective amount of one or more macrocyclic lactone compounds, including avermectin compounds, milbemycin compounds, or mixture thereof and a pharmaceutically acceptable carrier to the affected anorectal region of an individual suffering from hemorrhoid.

21 Claims, No Drawings

METHOD OF TREATING HEMORRHOIDS USING MACROCYCLIC LACTONE COMPOUND

FIELD OF THE INVENTION

The present invention relates to a method of treating hemorrhoids, more particularly a method of treating hemorrhoids using one or more macrocyclic lactone compounds, more specifically, one or more avermectin compounds or milbemycin compounds.

BACKGROUND OF THE INVENTION

Hemorrhoids are part of the normal human anatomy of the anal canal. In their physiological state they act as cushions composed of arterio-venous channels and connective tissue that aid the passage of stool. They become pathological or piles when swollen or inflamed. Hemorrhoids are classified according to their origin and the dentate line (pectinate line) serves as an anatomic border.

External hemorrhoids are dilations of anorectal vessels below the dentate line, which occur outside the anal verge (the distal end of the anal canal). Specifically, external hemorrhoids are varicosities of the veins draining the territory of the inferior rectal arteries, which are branches of the internal pudendal artery. External hemorrhoids commonly present with pain in the area of anus and often accompanied by swelling and irritation. External hemorrhoids are prone to thrombosis. If the vein ruptures and/or a blood clot develops, the hemorrhoid becomes a thrombosed hemorrhoid.

Internal hemorrhoids are dilations of anorectal vessels above the dentate line, which occur inside the rectum. Specifically, internal hemorrhoids are varicosities of veins draining the territory of branches of the superior rectal arteries. As this area lacks pain receptors, internal hemorrhoids are usually not painful and many people are not aware that they have the condition. However, internal hemorrhoids may bleed when irritated and untreated internal hemorrhoids can lead to two severe forms of hemorrhoids: prolapsed and strangulated hemorrhoids. Prolapsed hemorrhoids are internal hemorrhoids that are so distended that they are pushed outside the anus. If the anal sphincter muscle goes into spasm and traps a prolapsed hemorrhoid outside the anal opening, the supply of blood is cut off, and the hemorrhoid becomes a strangulated hemorrhoid.

Some hemorrhoids are regarded as mixed hemorrhoids (internal-external), arising from the inferior and superior hemorrhoidal plexi and their anastomotic connections, covered by mucosa in the superior part and skin in the inferior part, so they have somatic pain fibers.

Internal hemorrhoids are further classified into four grades according to the extent of prolapse. In first-degree hemorrhoids, the hemorrhoidal tissue protrudes into the lumen of the anal canal, but does not prolapse outside the anal canal. The veins of the anal canal are increased in size and number and may bleed at the time of evacuation. Second-degree hemorrhoids may prolapse beyond the external sphincter and be visible during evacuation but spontaneously return to lie within the anal canal. Third-degree hemorrhoids protrude outside the anal canal and require manual reduction, and fourth-degree hemorrhoids are irreducible and are constantly prolapsed.

A number of factors may lead to the formations of hemorrhoids, which include irregular bowel habits (constipation or diarrhea), exercise, gravity, low-fiber diet, increased intra-abdominal pressure (prolonged straining), pregnancy, obesity, prolonged sitting time, genetics, absence of valves within the hemorrhoidal veins, and aging.

Existing conservative treatments typically include life style modification, such as improving anal hygiene, increasing the intake of dietary fiber and fluids in the diet, and avoiding constipation or diarrhea, sitz baths, and rest; oral medication and topical treatment. In Europe and Asia, oral vasotopic drugs are used for treating hemorrhoids. It has been reported recently that oral micronized, purified flavonoid fraction rapidly relieves hemorrhoidal bleeding.

Many over the counter topical treatment products are available for hemorrhoids, which include pads, topical ointments, creams, gels, lotions, and suppositories. These preparations may contain various ingredients such as local anesthetics, corticosteroids, vasoconstrictors, antiseptics, keratolytics, protectants (such as mineral oils, cocoa butter), astringents (ingredients that cause coagulation, such as witch hazel), and other ingredients. Topical application of corticosteroids may ameliorate local perianal inflammation, however, long term use of high-potency corticosteroid creams can cause permanent damage and thinning of the perianal skin. Local anesthetics, such as 5% lidocaine ointment, decrease permeability to sodium ions in neuronal membranes, resulting in inhibition of depolarization, blocking transmission of nerve impulses. Preparation H®, one of the world's best-selling hemorrhoid treatments, contains 0.25% phenylephrine, a drug which constricts blood vessels. Preparation H may improve local symptoms but does not treat the underlying disorder and long term use is discouraged due to local irritation of the skin. Most of these topical treatment products help the patient maintain personal hygiene, and may alleviate symptoms of pruritus and discomfort. There are no prospective randomized trials suggesting that they reduce bleeding or prolapse.

Several nonsurgical procedures have been used to treat hemorrhoids, which function by ablation, sclerosis, or necrosis of mucosal tissues. These include rubber band ligation, sclerotherapy, and cauterization by using electrocautery, infrared radiation, or cryosurgery. When conservative medical management fails, surgeries have been used to treat severe hemorrhoids, for example, hemorrhoidectomy, doppler guided transanal hemorrhoidal dearterialization, and stapled hemorrhoidectomy. However, all surgical treatments are associated with some degree of complications, including bleeding, infection, anal strictures, and urinary retention due to the close proximity to the rectum of the nerves that supply the bladder.

The macrocyclic lactones (avermectins and milbemycins) are products or chemical derivatives thereof, of soil microorganisms belonging to the genus *Streptomyces*. The avermectin series and milbemycin series of compounds are very potent antiparasitic agents, useful against a broad spectrum of endoparasites and ectoparasites in mammals and also having agricultural utilities against various nematode and insect parasites found in and on crops and in soil. Compounds of this group include avermectins, milbemycins, and their semi-synthetic derivatives, for example, ivermectin, doramectin, emamectin, eprinomectin, selamectin, latidectin, milbemectin, moxidectin, nemadectin, milbemycin oxime, and lepimectin. These chemicals have been described, for example, in U.S. Pat. Nos. 3,950,360, 4,199,569, 4,879,749 and 5,268,710. The avermectins and, to a lesser extent, the milbemycins, have revolutionized antiparasitic and antipest control over the past few decades.

In terms of their mechanism of action as antiparasitic agents, the avermectins block the transmittance of electrical activity in nerves and muscle cells by activating voltage dependent membrane-bound proteins containing chloride channels. Chloride channel blockers in both insects and mammals are highly toxic convulsants causing a hyperexcitation of the nervous system through antagonism of the inhibitory neurotransmitter GABA. Avermectin compounds effectively block GABA stimulated uptake and cause a release of chloride-channel dependent neurotransmitters. Milbemycin compounds have a similar mechanism of action, but a longer half-life than the avermectins. Milbemycin compounds open glutamate sensitive chloride channels in neurons and myocytes of invertebrates, leading to hyperpolarization of these cells and blocking of signal transfer.

Ivermectin has been used as an antiparasitic agent to treat various animal parasites and parasitic diseases since mid-1980's. It is commercially available for animal use as Cardomec™ (for felines), Zimecterin® (for equines) and Ivomec® (for bovines) by MERIAL Limited, Duluth, Ga. The medicine is available in tablets, paste, or chewables for heartworm prevention, topical solution for ear mite treatment, or as oral or injectable solution for other parasite problems.

Ivermectin is also commercially available from Merck & Co., Inc for human use as Stromectol® for eradication of threadworm *Strongyloides stercoralis*, and for eradication of *Onchocerca volvulus*. The medicine is available in tablets and is orally administered by the patients. Magda et al. (*Amer. J. Trop. Med. Hyg.* 53(6) 1995 pp. 652-653) describe a method of topical application of ivermectin to treat head lice. U.S. Pat. No. 5,952,372 (to McDaniel) discloses a method of treating a form of rosacea associated with the ectoparasite Demodex by eliminating mites.

Recently, ivermectin has also been found useful in treating dermatological conditions. U.S. Pat. Nos. 6,133,310, 6,433, 006, 6,399,652, 6,399,651 and 6,319,945 (to Parks) disclose methods of treating acne rosacea, seborrheic dermatitis, acne vulgaris, transient acantholytic dermatitis, acne miliaris necrotica, acne varioliformis, perioral dermatitis, and acneiform eruptions by topically applying an avermectin compound, particularly ivermectin, to the affected areas.

Hemorrhoids are a common public health problem. Symptomatic hemorrhoids affect at least 50% of the American population at some time during their lives, with about 5% of the population suffering at any given time. Moreover, the existing topical medications for treating hemorrhoids have limited effects. Therefore, there is a need for more effective and improved topical compositions and minimal invasive methods for treating hemorrhoids.

SUMMARY OF THE INVENTION

In one embodiment, the present invention is directed to a method of treating hemorrhoid. The method comprises locally administering a composition comprising an effective amount of one or more macrocyclic lactone compounds including avermectin compounds, milbemycin compounds, or mixture thereof and a pharmaceutically acceptable carrier to the affected region of an individual suffering from hemorrhoid. The composition is administered intrarectally or topically to the anal verge and perianal skin of the individual one or more times.

In another embodiment, the present invention is directed to a composition comprising one or more avermectin compounds, milbemycin compounds, or mixtures thereof for treating hemorrhoid.

The avermectin compounds in the hemorrhoidal composition include avermectins, or avermectin derivatives such as ivermectin, ivermectin derivatives, emamectin, doramectin, selamectin, eprinomectin, or latidectin. The milbemycin compounds include milbemycins, or milbemycin derivatives such as moxidectin, nemadectin, milbemycin oxime, or lepimectin. Preferably, the hemorrhoidal composition comprises an effective amount of ivermectin.

The advantages of the present invention will become apparent from the following description in conjunction with exemplary embodiments of the invention.

DETAILED DESCRIPTION OF THE INVENTION

In one embodiment, the present invention provides a method of treating hemorrhoid using one or more macrocyclic lactone compounds. The method comprises locally administering a hemorrhoidal composition comprising an effective amount of one or more macrocyclic lactone compounds including avermectin compounds, milbemycin compounds, or mixture thereof and a pharmaceutically acceptable carrier to the affected anorectal region of an individual suffering from hemorrhoid.

In another embodiment, the present invention provides the use of one or more macrocyclic lactone compounds including avermectin compounds, milbemycin compounds, or mixture thereof in the preparation of a pharmaceutical composition intended for the treatment of hemorrhoid. Unless defined otherwise, all technical and scientific terms used herein have the same meaning as commonly understood by one having ordinary skills in the art to which the invention belongs.

The macrocyclic lactone compounds for the purpose of the present invention include avermectin compounds and milbemycin compounds. The avermectin compounds for the purpose of the present invention include avermectins and derivatives thereof, which include, but not limited to, avermectin $A_{1a}$, $A_{1b}$, $A_{2a}$, $A_{2b}$, $B_{1a}$, $B_{1b}$, $B_{2a}$, or $B_{2b}$, ivermectin and derivatives thereof, emamectin, doramectin, selamectin, eprinomectin, latidectin, or mixtures thereof. The milbemycin compounds for the purpose of the present invention include milbemycins and derivatives thereof, which include, but not limited to, milbemycins, moxidectin, nemadectin, milbemycin oxime, milbemectin, lepimectin, or mixtures thereof.

In one embodiment, the hemorrhoidal composition comprises one or more avermectin compounds and a pharmaceutically acceptable carrier or a medium which is suitable for application to the affected anorectal region, as described further in detail hereinafter. In another embodiment, the hemorrhoidal composition comprises one or more milbemycin compounds and a pharmaceutically acceptable carrier or a medium which is suitable for application to the affected anorectal region. Preferably, ivermectin is used in the hemorrhoidal composition.

The following molecular structure represents avermectins, which can be chemically converted to useful derivatives as discussed below.

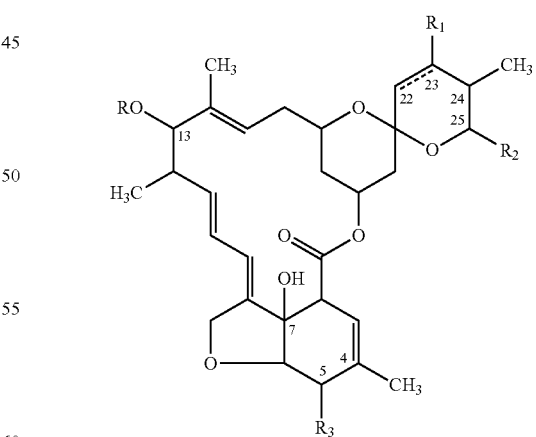

wherein the broken line at the 22-23 position represents an optional double bond; $R_1$ is hydroxy and is present only when the bond at the 22-23 position is a single bond; $R_2$ is isopropyl or sec-butyl; $R_3$ is methoxy or hydroxyl, and R is the 4'-(alpha-L-oleandrosyl)-alpha-L-oleandroside of the structure:

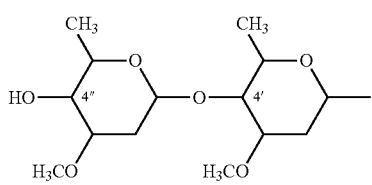 [SMILES: COC1CC(OC2C(C)OC(C)CC2OC)OC(C)C1O]

The naturally occurring avermectins are a series of 16-membered macrocyclic lactones isolated from fermentation products of *Streptomyces avermitilis*, a soil Actinomycete. There are eight different but closely related compounds produced by *Streptomyces avermitillis*, isolated in four pairs of homologue compounds with a major (a-component) and a minor (b-component) component, which are designated as avermectin $A_{1a}$, $A_{1b}$, $A_{2a}$, $A_{2b}$, $B_{1a}$, $B_{2b}$, $B_{2a}$, and $B_{2b}$. The mixture of avermectin $B_{1a}$ and $B_{1b}$, widely used insecticide and antihelmintic, are commonly referred to as abamectin. The production of these compounds is described in U.S. Pat. No. 4,310,519, which is incorporated herein by reference in its entirety. The structures of these eight individual compounds in reference to the above structural formula have been identified as follows:

|          | $R_1$       | $R_2$      | $R_3$   |
|----------|-------------|------------|---------|
| $A_{1a}$ | Double bond | sec-butyl  | —OCH₃   |
| $A_{1b}$ | Double bond | iso-propyl | —OCH₃   |
| $A_{2a}$ | —OH         | sec-butyl  | —OCH₃   |
| $A_{2b}$ | —OH         | iso-propyl | —OCH₃   |
| $B_{1a}$ | Double bond | sec-butyl  | —OH     |
| $B_{1b}$ | Double bond | iso-propyl | —OH     |
| $B_{2a}$ | —OH         | sec-butyl  | —OH     |
| $B_{2b}$ | —OH         | iso-propyl | —OH     |

The 22, 23-double bond of some avermectins may be selectively reduced to prepare ivermectin and its derivatives. Ivermectin, a member of avermectin compounds, is a semi-synthetic derivative of avermectins and is generally produced as a mixture of 22,23-dihydroavermectin $B_{1a}$ and 22,23-dihydroavermectin $B_{1b}$. The preparation of ivermectin and derivatives are disclosed in U.S. Pat. No. 4,199,569, which is incorporated herein by reference in its entirety.

The following structural formula shows the structures of ivermectin and its derivatives:

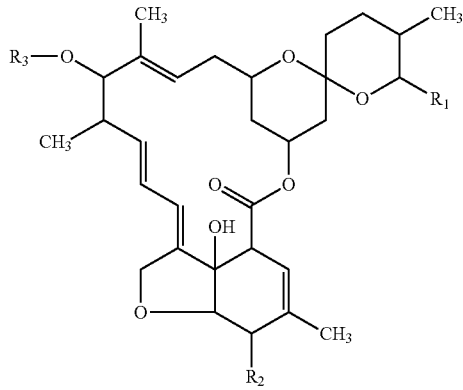

wherein $R_1$ is iso-propyl or sec-butyl; $R_2$ is methoxy, hydroxy or alkanoyloxy; $R_3$ is hydrogen; alkanoyl; alpha-L-oleandrosyl; 4'-alkanoyl-alpha-L-oleandrosyl; 4'-(alpha-L-oleandrosyl)-alpha-L-oleandrosyl; or 4''-alkanoyl-4'-(alpha-L-oleandrosyl)-alpha-L-oleandrosyl. Herein, the "alkanoyl" includes alkanoyl groups having 2 to 6 carbon atoms such as acetyl, propionyl, butyryl, and pivaloyl. Ivermectin and its derivatives shown above share profound anthelmintic, insecticidal, ectoparasiticidal and acaricidal activities.

Doramectin and eprinomectin are represented by the following structure:

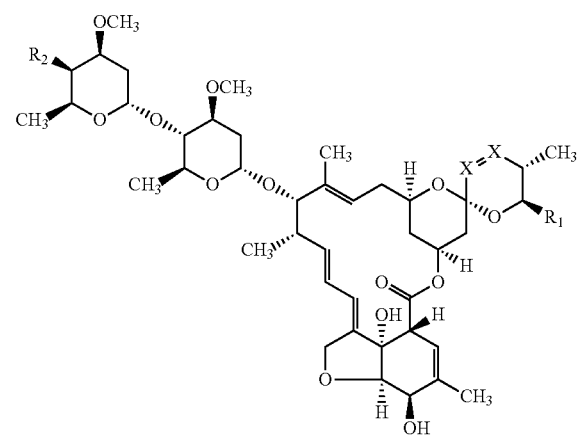

In doramectin, x=x is —CH=CH—; $R_1$ is —C₆H₁₀; $R_2$ is —OH. In eprinomectin, x=x is —CH=CH—; $R_1$ is —CH(CH₃)CH₂CH₃, or —CH(CH₃)₂; $R_2$ is —NHCOCH₃. These compounds are described in "Veterinary Parasitology", vol. 49, No. 1, July 1993, 5-15.

Selamectin has the following structure:

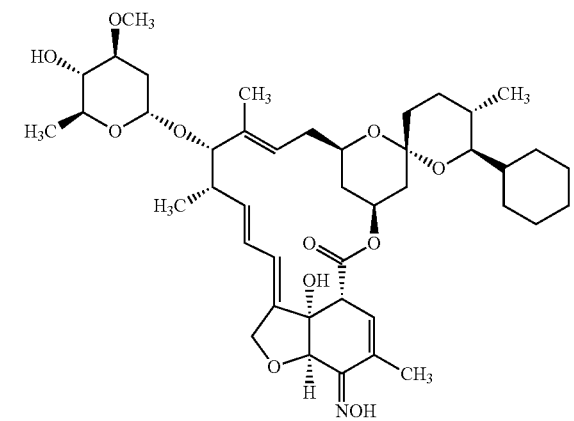

which is described in EP1142577A2 and WO 94/15944.

Emamectin has the following structure:

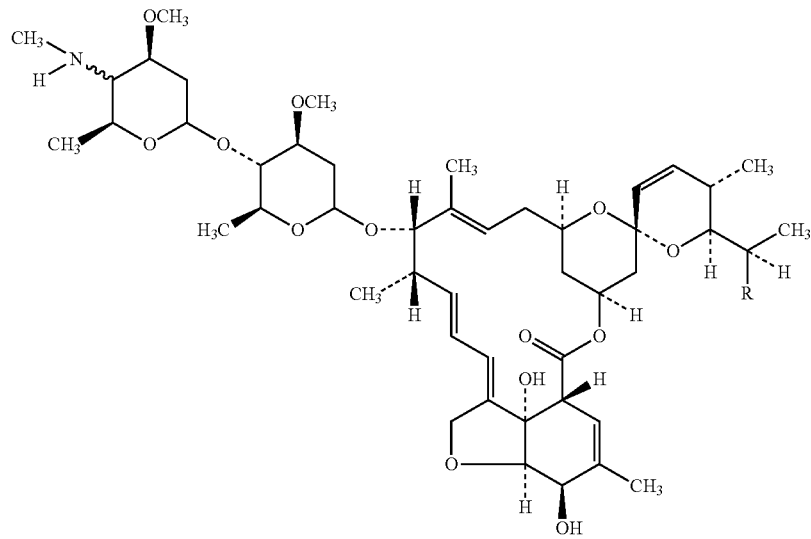

where R is —CH$_2$CH$_2$ or —CH$_3$. Emamectin and its salts are described in U.S. Pat. Nos. 4,874,749 or 5,288,710.

The structure of latidectin, which is a mixture of components A3 and A4, is shown below:

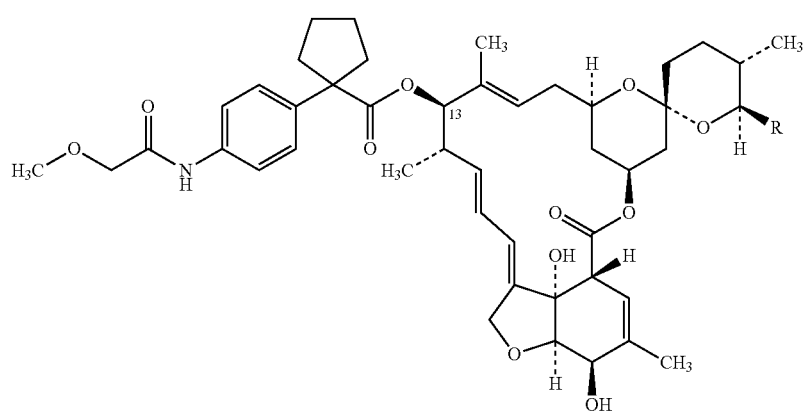

where component A3 has R=—CH$_2$CH$_3$, and component A4 has R=—CH$_3$.

Other avermectin derivatives are also known in the art. For example, the avermectins possess a disaccharide moiety at the C-13 position consisting of the alpha-L-oleandrosyl-alpha-L-oleandrosyl group. One or both of these saccharide groups may be removed as described in U.S. Pat. No. 4,206,205, and the produced aglycone derivatives have a hydroxy group at the 13-position. This group may be removed to form the 13-deoxy compound as described in U.S. Pat. Nos. 4,171,314 and 4,173,571, and the latter patent also describes the 13-halo derivatives. U.S. Pat. No. 5,077,308 describes avermectin aglycone derivatives which incorporate a ketal at C-13 position. The avermectins and derivatives have several hydroxy groups which may be acylated as described in U.S. Pat. Nos. 4,201,861. 5,055,454 describes avermectin derivatives in which position 13 of avermectin has been inverted from a normal alpha stereochemistry to the epimeric C-13 beta stereochemistry. U.S. Pat. No. 5,162,363 describes avermectin derivatives where the 23-position ring carbon atom is replaced with sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All aforementioned patents are incorporated herein by reference in their entirety.

All ivermectin compounds mentioned above share the 16-membered macrocyclic lactone ring and the spectrum of anti-parasitic biological activity of ivermectin, varying only in degree. It is expected that they also share the activity spectrum of ivermectin suitable for the purpose of the present invention.

Like avermectins, milbemycins are products of fermentation by *Streptomyces* species, isolated from the fermentation broth of *Streptomyces hygroscopicus* subsp. *aureolacrimosus*. They have same mode of action, but a longer half-life than the avermectins. Milbemycins include a series and β series, which were initially named as B-41 antibiotics and given the designation A$_1$, A$_2$, A$_3$, A$_4$, B$_1$, B$_2$, B$_3$, C$_1$ and C$_2$, as described in U.S. Pat. Nos. 3,950,360 and 3,984,564. The B-41 designations are still commonly used today. The correlation of the initial designation to the nomenclature of α and β series of some milbemycins is described in U.S. Pat. No. 4,144,352. Within the family, milbemycins $\alpha_{11}$, $\alpha_{14}$, $A_3$ and $A_4$ have been found having the most effective acaricidal activity. A mixture of milbemycins $A_3$ and $A_4$ is commercialized under the name milbemectin.

The following structural formula represents milbemectin and several potent derivatives of milbemycins:

| | $R_1$ | $R_2$ | $R_3$ |
|---|---|---|---|
| Milbemectin | —H, (β)-OH | —H, —H | —$CH_3$; —$CH_2CH_3$ |
| Milbemycin oxime | =NOH | —H, —H | —$CH_3$; —$CH_2CH_3$ |
| Moxidectin | —H, (β)-OH | =$NOCH_3$ | (Z)—C($CH_3$)=CH—CH($CH_3$)$_2$ |
| Nemadectin | —H, (β)-OH | —H, (α)-OH | (Z)—C($CH_3$)=CH—CH($CH_3$)$_2$ |

Further description of milbemycins and their derivatives can be found in "Avermectins and Milbemycins", Davies H. G. et al., 1986, Nat. Prod. Rep., 3, 87-121; "Synthesis of Milbemycins from Avermectins", Mrozik H. et al., 1983, Tetrahedron Lett., 24, 5333-5336; and U.S. Pat. Nos. 4,134,973 and 4,144,352.

A further derivative of milbemycin is lepimectin, which has the following structure:

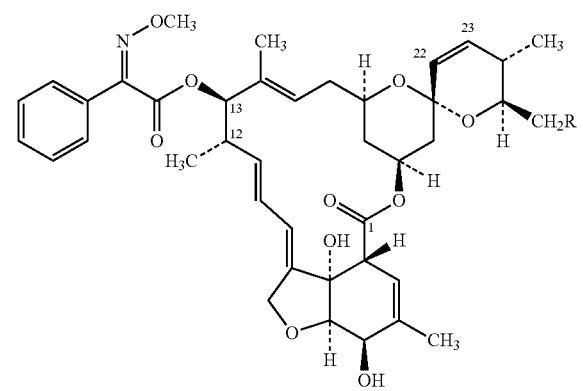

where R is —$CH_2CH_3$ (major component), and R is —$CH_3$ (minor component).

Both avermectins and milbemycins have macrocyclic lactone structures that are superimposable, they are produced by the same genus of soil dwelling organisms, they have the same mode of action, and they exert this action against the same nematode/acarine/insect spectrum of targets. It is expected that milbemycin compounds also share the activity spectrum of ivermectin suitable for the purpose of the present invention.

The concentration of the one or more avermectin compounds or the one or more milbemycin compounds in the hemorrhoidal composition for the purpose of the present invention can be greater than 0.001% weight by weight (w/w). In some embodiments, the concentration of the one or more avermectin compounds or the one or more milbemycin compounds in the composition is in a range from about 0.001% to about 10% (w/w), preferably from about 0.03% to about 5% (w/w), and more preferably from about 0.05% to about 3% (w/w). In a preferred embodiment, ivermectin is used. The concentration of ivermectin in the composition can be greater than 0.001% (w/w). In some embodiments, the concentration of ivermectin in the hemorrhoidal composition is from about 0.001% to about 10% (w/w), preferably from about 0.03% to about 5% (w/w), and more preferably from about 0.05% to about 3% (w/w). It has been found that the hemorrhoidal composition containing ivermectin at a concentration as low as 0.075% is effective, as illustrated in the examples hereinafter, in treating hemorrhoid. Such a low effective concentration is advantageous because it reduces risks of side effects and the possibility of triggering body's autoimmune responses.

Pharmaceutically acceptable carriers or media suitable for topical application to anorectal region are known to those having ordinary skill in the art. The hemorrhoidal composition can be in various forms, including, but not limited to, suppository, solution, spray, gel, ointment, or emulsion in the form of liquid suspension, lotion, or cream. The hemorrhoidal composition can also be integrated into medical dressing or toilet wipes. Furthermore, the hemorrhoidal composition can also be in the form of suspensions of microspheres or nanospheres, lipid or polymeric vesicles, or polymeric patches or hydrogels for controlled release.

In some embodiments, the hemorrhoidal composition is in the form of suppository. Typically, suppository includes one or more lipophilic agents. Suitable examples of lipophilic agents include, but not limited to, hydrogenated vegetable oils, cocoa butter, glycerinated gelatin, polyethylene glycols of different molecular weights, and fatty acid esters of polyethylene glycols. A suppository is placed in the rectal canal by inserting the suppository in a hardened state into the anus. The suppository is advanced past the anal sphincter where it is retained in the rectum of the patient. As the suppository is heated by the body, it melts and the macrocyclic lactone compound is released from the suppository to the surrounding mucosal tissue.

The mucosal tissue is an ideal site for the macrocyclic lactone compound to be delivered locally, because mucosal tissue has a very thin epithelium with minimal keratinized tissue, therefore, does not hinder the transport of the active component as compared to normal epidermal skin containing thick layers of keratinized tissues. Moreover, mucosal tissue is exposed to an abundant blood supply, which facilitates effective delivery into the hemorrhoids and the surrounding tissue.

In one exemplary embodiment, the hemorrhoidal composition is in a form of lotion having substantially neutral pH from about 6 to about 7. Example 1 provides an exemplary hemorrhoidal composition comprising ivermectin in a lotion.

As shown in the example, a commercially available moisturizing lotion manufactured by Galderma Laboratories, Inc. under the trade name Cetaphil® moisturizing lotion is used as the medium for ivermectin to form the hemorrhoidal composition. Cetaphil® moisturizing lotion contains purified water, glycerin, hydrogenated polyisobutene, cetearyl alcohol and ceteareth-20, *macadamia* nut oil, dimethicone, tocopheryl acetate, stearoxytrimethylsilane and stearyl alcohol, panthenol, farnesol, benzyl alcohol, phenoxyethanol, acrylates/C10-30 alkyl acrylate crosspolymer, sodium hydroxide, and citric acid.

In some embodiments, the hemorrhoidal composition is an emulsion with one or more macrocyclic lactone compound therein. More specifically, the hemorrhoidal composition comprises one or more avermectin compound or milbemycin compound, one or more solvents for the active agent, an oily phase, one or more surfactants as emulsifier, and water. The method of preparing an emulsion is known to those skilled in the art. The emulsion can be formulated into a solution, lotion, or cream. The emulsion can also be sprayable. Example 2 provides an exemplary hemorrhoidal composition, which is a cream containing 1% of ivermectin.

The hemorrhoidal composition in the form of ointments can be prepared using either an oleaginous base or medium or an absorbent base. The oleaginous base comprises fixed oils or hydrocarbons, such as white petrolatum or mineral oil. The absorbent base comprises an anhydrous substance or substances which can absorb water, for example anhydrous lanolin. Following formation of the base, the macrocyclic lactone compound is added to an amount affording the desired concentration to form the hemorrhoidal composition.

In some embodiments, the composition is in the form of a hydrogel. The water content in the gel has hydrating and cooling effect of the inflamed tissue. In some embodiments, the composition is in the form of liquid. The hemorrhoidal composition in the liquid form can be packaged into a squeezable liquid medicine dispenser with a rectal nozzle, such as an enema bottle.

The hemorrhoidal composition of the present invention described above is administered locally to the affected anorectal region, which includes administering intrarectally and/or administering topically to the anal verge and perianal skin. The phrase "administering intrarectally" used herein means administering into the rectum and anal canal, also referred to as anorectal canal. The term "anorectal region" used herein refers to the rectum and anal canal, the anal verge and the perianal skin.

In addition to the delivery of suppository and liquid composition described above, the hemorrhoidal composition in the form of lotion, cream, gel, or ointment can be instilled into the anorectal canal and applied topically to the anal verge and perianal skin with a gloved finger by the patient or using other tools that facilitate intrarectal delivery, for example cannula or nozzle. For external hemorrhoids, toilet wipes or medical dressing integrating the hemorrhoidal composition can also be conveniently used by the patient or medical professionals as needed.

The hemorrhoidal composition can be administered to the affected anorectal region one or more times a day, typically one to two times a day, when a pathological hemorrhoid condition occurs. When severe pain and swelling are present, the hemorrhoidal composition can be administered more frequently. It has been discovered by the inventors that application of the hemorrhoidal composition containing ivermectin to the anorectal region is effective in treating hemorrhoid, particularly at the early onset of the condition. A rapid resolution of the symptoms of hemorrhoids with only one or two application of an ivermectin lotion described in the examples to the affected region has been observed with many patients. Typically, the pain, swelling and irritation subside significantly within 24 hours after the application.

Preferably, the hemorrhoidal composition is administered to the affected anorectal region at early onset or prodrome of hemorrhoid. In medicine, a prodrome is an early symptom (or set of symptoms) that might indicate the start of a disease before specific symptoms occur. Prodromes may be non-specific symptoms or, in some instances, may clearly indicate a particular disease. In hemorrhoids, there is a prodrome involving a vague feeling of discomfort at the anorectal region, which may be triggered by early inflammation and tissue swelling. Typically, after a few episodes, a patient can recognize such feeling as indicating an impending recurrence of hemorrhoids. It has been found that if the hemorrhoidal composition containing ivermectin is applied at the time the patient recognizes the prodrome of hemorrhoid, only one application is sufficient to prevent a full blown episode of pathological hemorrhoid condition. In many instances, no further application or other treatments is needed after one single application of the instant hemorrhoidal composition. Such efficiency in the treatment of hemorrhoids is unexpected.

Examples 3 through 6 illustrate the effectiveness of the method of the present invention in treating hemorrhoid. As shown, after the patients suffering from internal or external hemorrhoids were treated with the instant hemorrhoidal composition containing 0.075% of ivermectin, a rapid resolution of the symptoms of pain, swelling, and irritation was typically observed within 24 to 48 hours.

Without being bound by any theoretical explanation and based on clinical observations by the inventors, it is believed that the efficacy of the hemorrhoidal composition and the method of the present invention in treating hemorrhoids is due in part to the anti-inflammatory property of ivermectin, as well as its antiseptic properties. It is believed that ivermectin is an effective anti-inflammatory agent, which blocks certain mediators of inflammation, therefore, diminishes symptoms caused by inflammation. This is substantially different from many existing hemorrhoidal medications, which merely treat the symptoms, but not the root cause, namely inflammation. Moreover, in view of the effect of ivermectin on neural system, it may also have some direct effects on the neural receptors in the anorectal region, which may contribute to the rapid pain relief observed clinically.

The hemorrhoidal composition containing ivermectin can be provided as a kit wherein the composition is packaged in a container. Instructions on how to use the hemorrhoidal composition in accordance with the present invention are included on or associated with the container, which provides detailed instructions for treating hemorrhoids. Optionally, the kit can further include application tools, such as disposable rectal nozzles, or finger cot gloves.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Composition A of an ivermectin lotion is prepared as follows: mix 0.04 g of Zimecterin® (manufactured by MERIAL Limited, Duluth, Ga.) which contains 1.87% ivermectin, sufficiently with 100 mg of Cetaphil® moisturizing lotion (manufactured by Galderma Laboratories, Inc.) to form an ivermectin lotion. The ivermectin concentration in the formed lotion is 0.075% (w/w).

Composition B of an ivermectin lotion is prepared as follows: mix 0.054 g of Zimecterin® containing 1.87% ivermectin sufficiently with 100 mg of Cetaphil® moisturizing lotion to form an ivermectin lotion. The ivermectin concentration in the formed lotion is 0.1% (w/w).

Other suitable compositions that can be made in accordance with Example 1 include ivermectin in the following concentrations: 0.01%, 0.05%, 0.12%, 0.15%, 0.2%, 0.5%, 1%, and 2% (w/w) with Cetaphil® moisturizing lotion as a medium. Other compatible commercial available lotions can also be used as a medium or carrier.

EXAMPLE 2

The following emulsion is prepared with the method known in the art.

| Ingredients | Percentage (% w/w) |
| --- | --- |
| Ivermectin | 1.0 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH to 6.3 |
| Water | qs 100 |

The emulsion is in the form of cream.

Operating with informed consent of individuals, individuals were treated with the hemorrhoidal composition and the method of the present invention for treating hemorrhoids, as described in Examples 3 to 6.

EXAMPLE 3

A 70-year old male, while serving in the army at age of 30, developed a red, hot clotted, internal/external hemorrhoid after strenuous exercise. The lesion had to be incised to evacuate the clot, and healing occurred over several days. However, since then the patient has had recurrent episodes of small internal and external hemorrhoids associated with an acute pain in the rectal vault. The patient was initially treated with Composition A of the ivermectin lotion of Example 1 when an acute episode occurred. The ivermectin lotion was applied intrarectally and around anus using a gloved finger. The treatment resulted in prompt relief of pain and the lesions subsided in one to two days. The patient learned to recognize the vague uncomfortable prodrome as an impending, inflamed hemorrhoid, then immediately applied the lotion. The discomfort cleared overnight, usually requiring only one dose. After the treatment with the ivermectin lotion for several episodes occurred in a period of more than two years, the patient reports now that the frequency of attacks has decreased in comparison to the historical recurrent pattern prior to using the ivermectin treatment.

EXAMPLE 4

A 50-year old white female with a long history of internal and external hemorrhoids since childbirth in 1987. None of the prior therapies had been satisfactory. A sample of Composition A of the ivermectin lotion of Example 1 was provided to the patient with instruction of applying intrarectally and externally to the affected region. The patient reported prompt resolution of the symptoms of pain and irritation in 48 hours after application of the ivermectin lotion twice a day in a recurrent episode. Moreover, the patient was pleased that the lotion was not as messy as existing commercial products.

EXAMPLE 5

A 48-year old male physician was seen with recurrent hemorrhoids, which was poorly responsive to standard treatments with over the counter and prescription topical medications (steroids and anti-inflammatory medications). The patient was given a trial of Composition A of the ivermectin lotion of Example 1 to instill high into the rectal vault. A prompt relief of the symptoms was observed in two hours and the patient was amazed with the effect of the treatment. A sample of the ivermectin lotion was provided to the patient for home use twice a day for recurrent episodes.

EXAMPLE 6

A 24-year old white female with a long history of small, painful, internal rectal vault hemorrhoids with occasional anal rim hemorrhoids. The patient was treated with topical application of Composition B of the ivermectin lotion of Example 1 to the affected region twice a day. The treatment provided prompt pain relief and dissipation of the hemorrhoids in 24 to 48 hours. Subsequently, the patient was taught to recognize the signs of impending recurrence and to treat promptly for effective self-management of the chronic condition. In follow ups with the patient, the patient noted that since following the instruction of prompt application of the ivermectin lotion at the time of recognizing the prodrome, the frequency of hemorrhoid has decreased dramatically.

In the above described informal trials, no adverse side effects or contra-indications were observed among the patients. The patients had no complaints of irritation, sensitivity or discomfort at the applied regions originating from the treatment.

Each patent, patent application, publication, text and literature article or report cited or indicated herein is hereby expressly incorporated by reference in its entirety.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of treating hemorrhoid comprising locally administering an effective amount of one or more macrocyclic lactone compound to affected region of an individual suffering from hemorrhoid, wherein said macrocyclic lactone compound is avermectin compound, milbemycin compound, or mixtures thereof.

2. The method of claim 1, wherein said macrocyclic lactone compound is administered intrarectally to the individual.

3. The method of claim 1, wherein said macrocyclic lactone compound is administered topically to the anal verge and the perianal skin to the individual.

4. The method of claim 1, wherein said macrocyclic lactone compound is applied with a gloved finger or using a nozzle.

5. The method of claim 1, wherein said macrocyclic lactone compound is administered one to more times a day to the affected region.

6. The method of claim 1, wherein said hemorrhoid is an internal or external hemorrhoid.

7. The method of claim 1, wherein said avermectin compound is selected from the group consisting of avermectins, ivermectin, emamectin, doramectin, selamectin, eprinomectin, and latidectin.

8. The method of claim 1, wherein said milbemycin compound is selected from the group consisting of milbemycins, moxidectin, nemadectin, milbemycin oxime, milbemectin, and lepimectin.

9. The method of claim 1, wherein said macrocyclic lactone compound is from about 0.001% to about 10% (w/w) in a composition.

10. The method of claim 1, wherein said macrocyclic lactone compound is from about 0.03% to about 5% (w/w) in a composition.

11. The method of claim 1, wherein said macrocyclic lactone compound is from about 0.05% to about 3% (w/w) in a composition.

12. The method of claim 1, wherein said avermectin compound is ivermectin.

13. The method of claim 12, wherein said ivermectin is greater than 0.001% (w/w) in a composition.

14. The method of claim 12, wherein said ivermectin is from about 0.001% to about 10% (w/w) in a composition.

15. The method of claim 1, wherein said macrocyclic lactone compound is in a suppository.

16. The method of claim 1, wherein said macrocyclic lactone compound is in a lotion, cream, gel, solution, ointment, or spray.

17. The method of claim 1, wherein said macrocyclic lactone compound is integrated in a medical dressing or toilet wipes.

18. The method of claim 1, wherein applying said macrocyclic lactone compound to the affected area rapidly relieves pain, swelling and irritation associated with the hemorrhoid, and/or dissipates the hemorrhoid.

19. The method of claim 18, wherein applying said macrocyclic lactone compound to the affected area relieves pain, swelling and irritation associated with the hemorrhoid, and/or dissipates the hemorrhoid within 24 to 48 hours.

20. The method of claim 1, wherein applying said macrocyclic lactone compound to the affected area decreases frequency of reoccurrence of the hemorrhoid.

21. The method of claim 1, wherein applying said macrocyclic lactone compound to the affected area at prodrome of the hemorrhoid prevents a full blown episode of pathological hemorrhoid condition.

* * * * *